United States Patent
Chapman et al.

(10) Patent No.: US 6,942,685 B2
(45) Date of Patent: Sep. 13, 2005

(54) APPARATUS FOR TANNING FEET AND ANKLES

(75) Inventors: Donna Riggs Chapman, Burlington, KY (US); John Lemert, Fort Wayne, IN (US); Jeffrey Walker, Fort Wayne, IN (US)

(73) Assignee: Golden Feet Ltd., Cincinnati, OH (US)

( * ) Notice: Subject to any disclaimer, the term of this patent is extended or adjusted under 35 U.S.C. 154(b) by 0 days.

(21) Appl. No.: 10/703,055

(22) Filed: Nov. 6, 2003

(65) Prior Publication Data

US 2004/0098071 A1 May 20, 2004

Related U.S. Application Data

(60) Provisional application No. 60/424,193, filed on Nov. 6, 2002.

(51) Int. Cl.[7] ................................................. A61N 5/06
(52) U.S. Cl. ................................ 607/91; 88/93; 88/94
(58) Field of Search .......................... 607/88–91, 93–95

(56) References Cited

U.S. PATENT DOCUMENTS

| | | | | |
|---|---|---|---|---|
| 2,054,332 A | * | 9/1936 | Lower et al. .................. | 607/91 |
| 5,466,248 A | * | 11/1995 | Whitson-Newman ........ | 607/88 |
| 6,273,906 B1 | * | 8/2001 | Swanson ...................... | 607/91 |
| 6,443,978 B1 | * | 9/2002 | Zharov ......................... | 607/91 |
| 6,676,687 B2 | * | 1/2004 | Stoppler ....................... | 607/94 |
| 6,761,730 B1 | * | 7/2004 | Johnson et al. ............... | 607/94 |
| 6,776,790 B1 | * | 8/2004 | Maruyama et al. ........... | 607/94 |
| D497,003 S | * | 10/2004 | Craig et al. ................ | D24/210 |
| 2003/0060853 A1 | * | 3/2003 | Unvert et al. ................. | 607/20 |

OTHER PUBLICATIONS

SunCo Distributors' "HL Classic Legs" leg tanner brochure, see Appendix A.*

Wolf Tanning Systems "Legacy™" leg tanner brochure, see Exhibit B.*

* cited by examiner

*Primary Examiner*—A. Farah
(74) *Attorney, Agent, or Firm*—WM. Cates Rambo

(57) ABSTRACT

A cover equipped to hold three pairs of ultraviolet tanning lamps is pivotally attached to a base in which the ballasts, starters, timer and other electrical equipment for energizing the lamps are housed. A transparent acrylic bezel is provided for each pair of tanning lamps to protect the user's feet. A pair of ankle receiving openings are provided in the cover, and a foot-receiving platform is provided in the base.

14 Claims, 2 Drawing Sheets

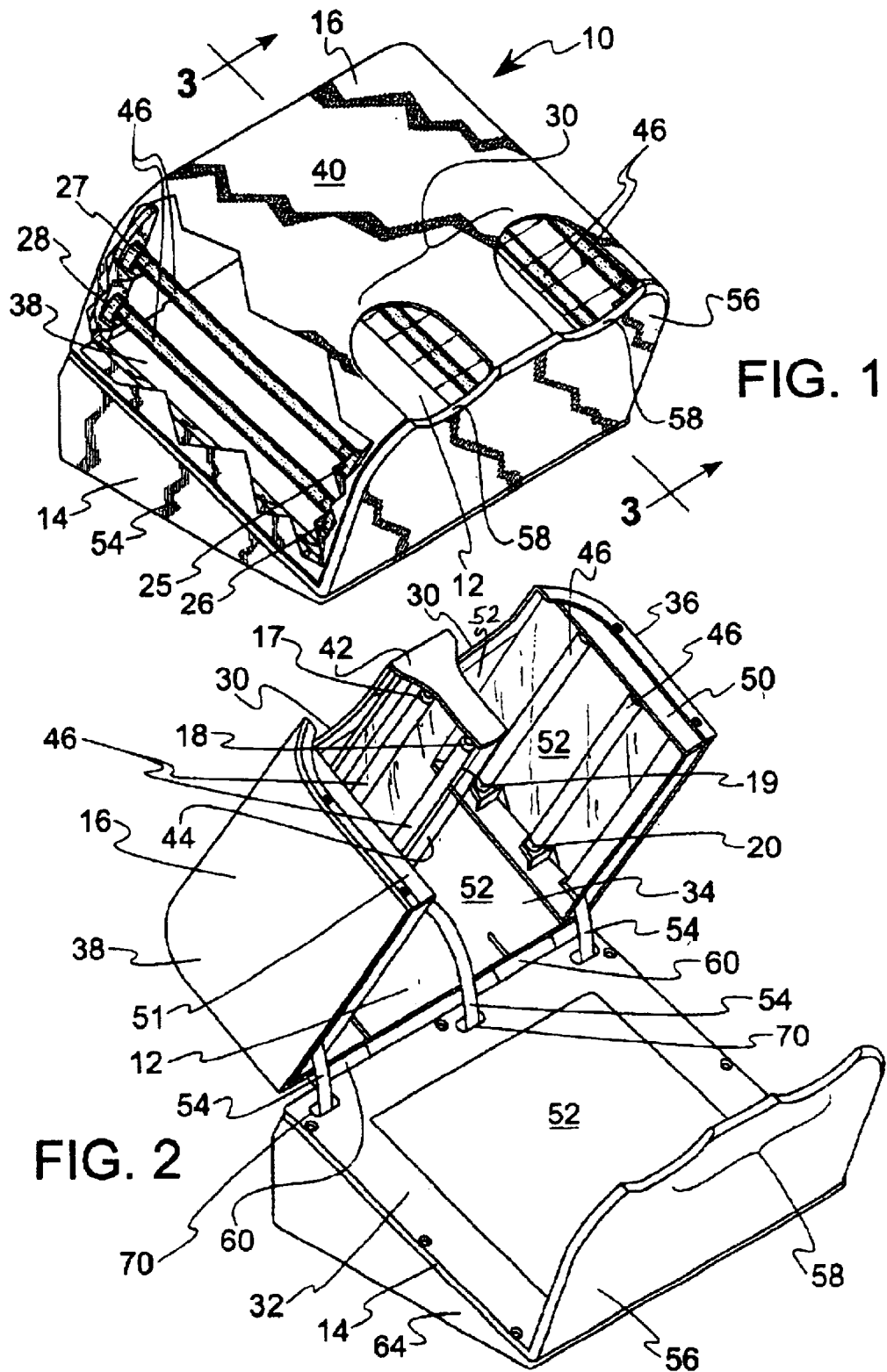

APPARATUS FOR TANNING FEET AND ANKLES

RELATED APPLICATION

A claim is hereby made to the benefit of U.S. Provisional Application No. 60/424,193 filed Nov. 6, 2002.

BACKGROUND OF THE INVENTION

The present invention relates to tanning devices and more particularly to those which comprise an enclosure and a light source.

Tanning beds are ill suited for those who want to tan small areas of their bodies. Golfers and tennis players, for example, have little need for a tanning bed, since their arms, legs and faces get as much exposure to the sun's rays as those individuals choose to permit. Their ankles and feet, however, rarely see the light of day on the golf course or tennis court. For those who expose their feet or ankles in public when not engaged in their sport of choice, the contrast between tanned legs and untanned ankles and feet can be disconcerting.

Accordingly, the present inventor was faced with the problem of developing a device that would tan just the ankles and upper portions of the user's feet.

BRIEF SUMMARY OF THE INVENTION

The present apparatus for tanning a user's feet and ankles basically comprises an enclosure and a plurality of tanning lamp-receiving sockets arrayed within the enclosure. The enclosure is defined by a base and by a cover which is movable relative to the base. The cover is provided with at least one ankle-receiving opening and the base is provided with a foot-receiving platform.

BRIEF DESCRIPTION OF THE DRAWINGS

FIG. 1 is a perspective view of an apparatus for tanning feet and ankles according to the present invention, with the cover in a closed position;

FIG. 2 is a perspective view of the present apparatus with the cover in an open position.

DETAILED DESCRIPTION OF THE PREFERRED EMBODIMENT

Figure 3:
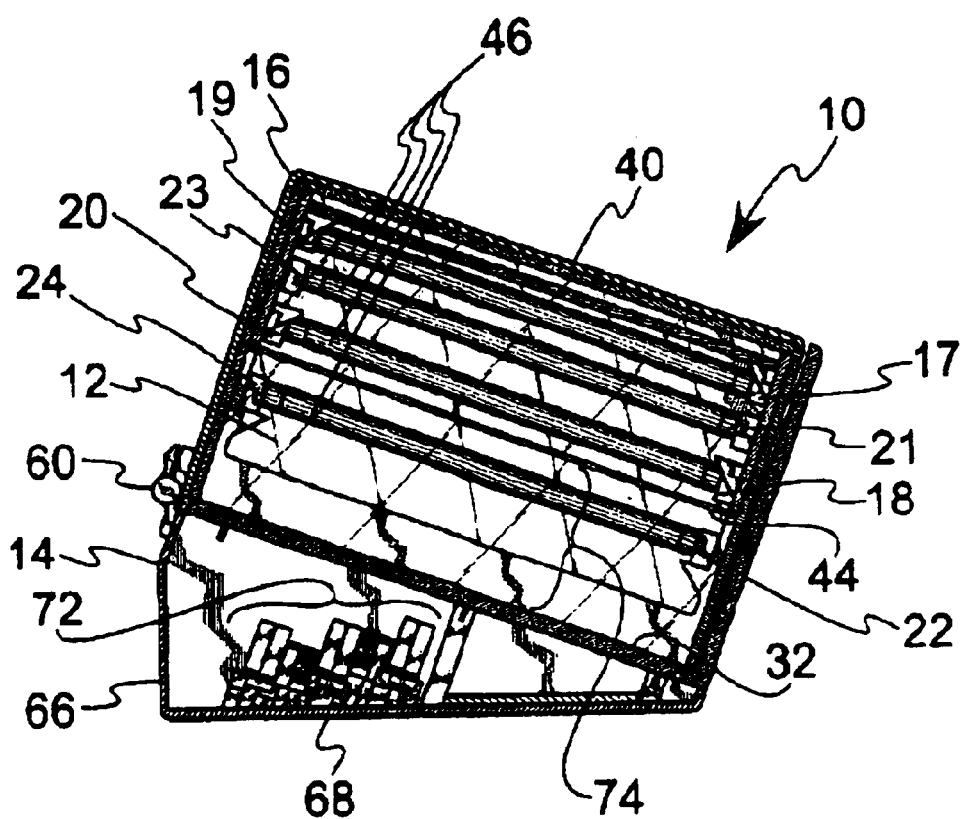
FIG. 3 is a sectional view of the present apparatus taken along line 3—3 of FIG. 1.

As indicated in FIGS. 1, 2 and 3, an apparatus, generally designated 10, according to the present invention comprises an enclosure 12 and a plurality of tanning lamp-receiving sockets 17, 18 arrayed within the enclosure 12. The enclosure 12 is defined by a base 14 and by a cover 16 which is movable relative to the base 14.

The cover 16 is provided with at least one, preferably a pair, of ankle-receiving openings 30, and the base 14 is provided with a foot-receiving platform 32.

As illustrated in FIGS. 1, 2 and 3, the cover or canopy 16 preferably includes the following features. It is injection molded or otherwise formed from synthetic resin material with a back wall 34, opposing side walls 36, 38 and a top 40. The ankle-receiving openings 30 in the cover 16 are formed in spaced relation to one another in a front portion of the top 40. A divider 42 projects downwardly from the front portion of the top 40 between the ankle-receiving openings 30. Upper and lower lamp-receiving sockets 17, 18 are supported by the interior side of the divider 42, and corresponding sockets 19, 20 (FIG. 3) are supported by the interior side of the back wall 34. A transparent U-shaped acrylic bezel 44 extends from the divider 42 to the back wall 34 in overlying relation to the lamp sockets 17–20 and serves as a housing for the 10 watt ultraviolet tanning lamps 46 mounted in the lamp-receiving sockets 17–20 and as a barrier to prevent the user's feet from touching the lamps 46. Lamp sockets 21–24 are supported at the front and rear of one of the opposing side walls 36 and are disposed to receive two 10 watt ultraviolet tanning lamps 46. A generally L-shaped acrylic bezel 50 extends from the front to the rear of the side wall 36 in overlying or covering relation to the 10 watt ultraviolet tanning lamps 46 and the lamp sockets 17–20 to protect the user's feet. Lamp sockets 25–28 are supported at the front and rear of the opposite side wall 38 and are disposed to receive two 10 watt ultraviolet tanning lamps 46. A generally L-shaped acrylic bezel 51 extends from the front to the rear of the side wall 38 in overlying or covering relation to the 10 watt ultraviolet tanning lamps 46 and the lamp sockets 25–28 to protect the user's feet. Sheets of reflective material 52 are mounted on the interior surfaces of the top 40, back wall 34, and opposing side walls 36, 38 of the cover. Flexible conduits 54 for electrical wiring extend generally vertically along the back wall 34 of the cover 16 to the rear lamp sockets 19,20 and 27,28 of the opposing side walls 36, 38 and to the rear sockets 19,20 of the central lamp assembly.

As further illustrated in FIGS. 1, 2 and 3, the base or lower housing 14 preferably includes the following features. A front wall 56 extends upwardly from a front edge of the platform 32 at approximately a 90° angle. An upper edge portion of the front wall 56 is formed with a pair of scallops 58 which correspond in position to the ankle-receiving openings 30 in the cover. The rest of the edge portions of the front wall 56 are disposed to engage corresponding front portions of the cover 16. The lower edges of the sides 36, 38 and back wall 34 of the cover are configured to be aligned with the outer edges of the platform 32 when the cover 16 is in the closed position (FIG. 1). A sheet of reflective material 52 is mounted on the platform 32, and openings 60 are provided in the platform to receive the conduits 54. In addition to the platform 32 and front wall 56, the base 14 is provided with a pair of forwardly inclined side walls 62, 64, a rear wall 66 (FIG. 3) and a bottom wall 68 (FIG. 3). The rear wall 66 and the forwardly inclined side walls 62, 64 support the platform 32 and the front wall 56 in a tilted position which allows the user to extend his or her legs somewhat and rest the user's lower calves on the scalloped edges 58 of the front wall 56 while using the device 10. A pair of hinges 70 (FIGS. 2 and 3) are secured to the back wall 66 of the base 14 and to the back wall 34 of the cover 12 so that the cover 12 is pivotally mounted on the base 14 to move between the closed and opened positions illustrated in FIGS. 1 and 2, respectively.

As illustrated in FIG. 3, electronic ballasts, starters, fuses, a timer, a power cord and associated wiring and circuitry, collectively designated 72, are preferably housed in the base 14. The central transparent bezel 44 and the associated pairs of lamps 46 and lamp sockets 17-20 are preferably disposed higher in the cover 16 than the side wall bezels 50, 51 and associated lamps 36 and sockets 21–24 and 25–28. A space 74 is preferably provided between the bottom of the central bezel 44 and the foot platform 32 when the cover 16 is in the closed position. In this manner, the user is able to move his or her feet about in the enclosure 12.

While the preferred embodiment of the present feet and ankle tanning apparatus has been illustrated and described in substantial detail, the foregoing disclosure is not intended to unduly limit or restrict the spirit of the invention or the scope of the following claims.

We claim:

1. Apparatus for tanning a user's feet and ankles comprising an enclosure and a plurality of lamp sockets arrayed within the enclosure, said enclosure being defined by a base provided with a foot-receiving platform and by a cover movable between opened and closed positions relative to said base, said cover being provided with a back wall, a pair of opposing side walls and a top, said top having at least one ankle-receiving opening.

2. The apparatus according to claim 1, wherein reflective material is mounted on the interior surfaces of the top, back wall, and opposing sidewalls of the cover.

3. The apparatus according to claim 1, wherein a pair of ankle-receiving openings are disposed in spaced relation to one another in a front portion of the top of the cover, said top being of one-piece construction.

4. The apparatus according to claim 3, wherein a divider projects downwardly from the front portion of the top between the ankle-receiving openings.

5. The apparatus according to claim 4, wherein first and second lamp sockets are supported by the divider, and wherein third and fourth lamp sockets are supported at the back wall of the cover.

6. The apparatus according to claim 5, wherein a first transparent housing extends longitudinally from the divider to the back wall of the cover in overlying relation to the first, second, third and fourth lamp sockets, said first transparent housing having at least one longitudinally extending edge portion.

7. The apparatus according to claim 6, wherein a space is provided between the first transparent housing and the foot-receiving platform with the cover in the closed position.

8. The apparatus according to claim 1, wherein fifth and sixth lamp sockets are supported at a front portion of one of the side walls and wherein seventh and eighth lamp sockets are supported at the back wall of the cover.

9. The apparatus according to claim 8, wherein a second transparent housing extends from the front portion of said side wall to the back wall in covering relation to the fifth, sixth, seventh and eighth lamp sockets.

10. The apparatus according to claim 1, wherein ninth and tenth lamp sockets are supported at a front portion of the opposite side wall and wherein eleventh and twelfth lamp sockets are supported at the back wall of the cover.

11. The apparatus according to claim 10, wherein a third transparent housing extends from the front portion of said opposite side wall to the back wall in covering relation to the ninth, tenth, eleventh and twelfth lamp sockets.

12. The apparatus according to claim 1, wherein the base is provided with a substantially closed front wall extending upwardly from the platform.

13. The apparatus according to claim 12, wherein an upper edge portion of the front wall is formed with at least one scallop corresponding in position to the at least one ankle-receiving opening in the cover.

14. The apparatus according to claim 12, wherein edge portions of the front wall are disposed to releasably engage front portions of the cover and wherein lower edges of the sidewalls of the cover are disposed to releasably engage outer edges of the platform with the cover is in the closed position.

* * * * *